(12) United States Patent
Beattie et al.

(10) Patent No.: US 9,750,809 B2
(45) Date of Patent: Sep. 5, 2017

(54) CANCER TREATMENT (71) Applicant: MOREX DEVELOPMENT PARTNERS LLP, London, Greater London (GB)

(72) Inventors: Christopher Beattie, Farnham (GB); Anne Wadsworth, Wokingham (GB); James Rennie, Camberley (GB)

(73) Assignee: MOREX DEVELOPMENT PARTNERS LLP C/O BLUE ROCK SERVICES, London (GB)

( * ) Notice: Subject to any disclaimer, the term of this patent is extended or adjusted under 35 U.S.C. 154(b) by 58 days.

(21) Appl. No.: 14/413,949

(22) PCT Filed: Jul. 11, 2013

(86) PCT No.: PCT/EP2013/064735
§ 371 (c)(1),
(2) Date: Jan. 9, 2015

(87) PCT Pub. No.: WO2014/009496
PCT Pub. Date: Jan. 16, 2014

(65) Prior Publication Data
US 2015/0157712 A1    Jun. 11, 2015

(30) Foreign Application Priority Data

Jul. 12, 2012 (GB) .................................. 1212409.5

(51) Int. Cl.
| | | |
|---|---|---|
| A61K 41/00 | (2006.01) | |
| A61K 31/555 | (2006.01) | |
| A61K 31/409 | (2006.01) | |
| A61K 33/34 | (2006.01) | |
| A61K 51/04 | (2006.01) | |
| C07D 487/22 | (2006.01) | |
| A61N 5/10 | (2006.01) | |

(52) U.S. Cl.
CPC ........ *A61K 41/0038* (2013.01); *A61K 31/409* (2013.01); *A61K 31/555* (2013.01); *A61K 33/34* (2013.01); *A61K 41/0057* (2013.01); *A61K 41/0095* (2013.01); *A61K 51/0485* (2013.01); *A61N 5/10* (2013.01); *C07D 487/22* (2013.01); *A61N 2005/1098* (2013.01)

(58) Field of Classification Search
None
See application file for complete search history.

(56) References Cited

U.S. PATENT DOCUMENTS

| 9,358,290 B2 * | 6/2016 | Beattie ............... A61K 41/0038 |
| 2005/0287073 A1 | 12/2005 | Wu et al. |
| 2008/0131376 A1 | 6/2008 | Miura et al. |
| 2008/0233047 A1 | 9/2008 | Miura et al. |

FOREIGN PATENT DOCUMENTS

| JP | 2005504012 | 2/2005 |
| JP | 2006298897 | 11/2006 |
| JP | 2010511704 | 4/2010 |
| WO | WO 2007/050564 A2 | 5/2007 |
| WO | WO 2007/050564 A3 | 5/2007 |

OTHER PUBLICATIONS

CAS Registry record 1030303-53-7 (retrieved May 2016).*
"Pharmacokinetics & Pharmacodynamics: Dose Selection & the Time Course of Drug Action" by Holford et al., pp. 34-49 in Basic & Clinical Pharmacology, 7th Edition by Katzung (Ed.), Appleton & Lange (Stamford, Connecticut) (1998).*
"Boron Neutron Capture Therapy for Glioblastoma Multiforme: Interim Results from the Phase I/II Dose-Escalation Studies" by Chanana et al., Neurosurgery 44, 1182-93 (1999).*
Daryoush Shanbazi-Gahrouei et al., "Synthesis and Application of New Gadolinium-Porphyrins as Potential MR Imaging Contrast Agents for Cancer Detection in Nude Mice", Iranian Biomedical Journal, vol. 5, (2&3), pp. 87-95, (2001).
Erica L. Kreimann et al., "Biodistribution of a Carborane-Containing Porphyrin as a Targeting Agent for Boron Neutron Capture Therapy of Oral Cancer in the Hamster Cheek Pouch", Archives of Oral Biology, vol. 48, Issue 3, pp. 223-232, (2003).
Shinji Kawabata et al., "Convection Enhanced Delivery of Carboranylporphyrins for Neutron Capture Thereapy of Brain Tumors", Journal of Neuro-Oncology, vol. 103, No. 2, pp. 175-185, (2010).
International Preliminary Report on Patentability for International Patent Application No. PCT/EP2013/064735 mailed Nov. 5, 2014 from the European Patent Office.
International Search Report for International Patent Application No. PCT/EP2013/064735 mailed Nov. 4, 2013 from the European Patent Office.

(Continued)

*Primary Examiner* — Theodore R West
(74) *Attorney, Agent, or Firm* — Finnegan, Henderson, Farabow, Garrett & Dunner LLP (57) ABSTRACT

A carborane-comprising porphyrin of Formula (1) is provided for use in cancer therapy that extends the period of time between the doses required while the patient is undergoing radiation therapy. The compound can be given not more often than once every 2 or more weeks, avoiding repeated administration, while radiation therapy can continue regularly.

(1)

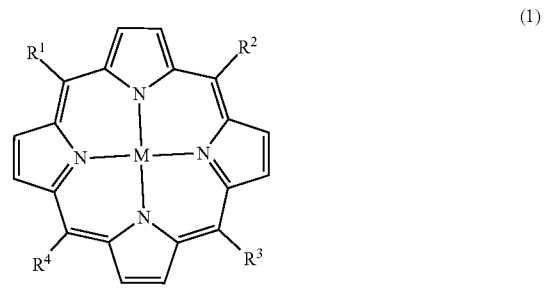

30 Claims, 3 Drawing Sheets

(56) References Cited

OTHER PUBLICATIONS

Written Opinion of the International Searching Authority for International Patent Application No. PCT/EP2013/064735 mailed Nov. 4, 2013 from the European Patent Office.
Patents Act 1977: Search Report under Section 17(5) for corresponding GB Patent Application No. GB 1212409.5 mailed Nov. 8, 2012 from the GB Intellectual Property Office.
Cohen et al., "Modification of Radiosensitivity by Porphyrins II. Transplanted Rhabdomyosarcoma in Mice," *Cancer Research*, 26(1): 1769-1773 (1966).
Japanese Office Action for Japanese Patent Application No. 2015-520999 dated Jul. 7, 2015, 13 pages.
Tibbits et al., "Plasma Pharmacokinetics and Tissue Biodistribution of Boron Following Administration of a Boronated Porphyrin in Dogs," *Journal of Pharmaceutical Sciences*, 89(4): 469-477 (2000).

* cited by examiner

CANCER TREATMENT

FIELD

The present invention relates to the treatment of cancer using radiation therapy.

BACKGROUND

Many approaches can be taken in the treatment of cancer. One approach is the use of radiosensitisers along with radiation therapy. This two-pronged approach increases the likelihood of success of the cancer therapy. Radiosensitisers are compounds which when administered to the patient make the tumour more sensitive to radiotherapy or act as an oxygen mimic such that they increase the free radicals available following the ionising radiation. The latter type of compound results in the repair mechanisms within the cell being overwhelmed and cell death occurring.

Radiosensitisers involve time-consuming administration by a specialist, which is expensive for the medical institution involved in the treatment. The radiosensitisers are generally given intravenously or by injection in large fluid volumes that take a significant amount of time to administer and a single dose may involve administration over more than one day. The invasive nature of the administration can lead to multiple puncture sites that are at risk of infection.

Most importantly, administration of the radiosensitiser is distressing to the patient. However, in order to maintain therapeutically effective levels within the tumours radiosensitisers that enhance sensitivity to radiation may be administered on a daily basis. Daily irradiation takes place afterwards. Some cytotoxics that are used as radiosensitisers may be administered less frequently, generally once every 3-4 days or at least once per week (e.g. Cisplatin).

Compared to the administration of the radiosensitiser, irradiation is a relatively simple step. Irradiation often takes place for five days and then the patient has two days off before the cycle is repeated until the course of treatment devised by the patient's clinician is finished. The length of the course of treatment will depend, among other things, upon the patient, the type of cancer and the stage of cancer.

US 2008/0131376 describes low toxicity carborane-containing porphyrin compounds with halide, amine or nitro groups and methods and their use, particularly in boron neutron capture therapy (BNCT), X-ray radiation therapy (XRT) and photodynamic therapy (PDT) for the treatment of tumours of the brain, head and neck and surrounding tissue. Using these carborane-containing porphyrin compounds in methods of tumour imaging and/or diagnosis such as MRI, SPECT or PET is also described.

Daryoush Shahbazi-Gahrouei et al. "Synthesis and Application of New Gadolinium-Porphyrins as Potential MR Imaging Contrast Agents for Cancer Detection in Nude Mice" *Iranian Biomedical Journal* 5 (2 & 3), pp 87-95 (April and July 2001) discloses the structures of Gd-hematoporphyrin and Gd-tetra-carboranylmethoxyphenyl-porphyrin and notes their selective accumulation in human melanoma xenografts on nude mice. The use of these compounds as a dual probe for MRI and BNCT was suggested.

Kreimann et al. "Biodistribution of a carborane-containing porphyrin as a targeting agent for Boron Neutron Capture Therapy of oral cancer in the hamster cheek pouch" *Archives of Oral Biology*, Vol. 48, Issue 3, Pages 223-232, March 2003 discloses the use of CuTCPH, a lipophilic, carborane-containing tetraphenylporphyrin, in the hamster oral cancer model and considers its biodistribution after peritoneal administration. Kreimann et al. also suggest that this compound might be useful in BNCT.

WO 2007/050564 describes boron-containing tetraphenylporphyrin compounds for use in BNCT of tumours, radiotherapy of tumours and PDT of tumours.

US 2005/0287073 describes low toxicity carborane-containing 5,10,15,20-tetraphenylporphyrin compounds and methods for their use particularly in BNCT and PDT for the treatment of tumours of the brain, head, neck and surrounding tissue. US 2005/0287073 also describes using these carborane-containing tetraphenylporphyrin compounds in methods of tumour imaging and/or diagnosis such as MRI, SPECT and PET.

US 2008/0233047 describes low toxicity halogenated, carborane-containing 5,10,15,20-tetraphenylporphyrin compounds and methods for their use particularly in BNCT and PDT for the treatment of tumours of the brain, head and neck and surrounding tissue. US 2008/0233047 also describes using these halogenated, carborane-containing tetraphenylporphyrin compounds in methods of tumour imaging and/or diagnosis such as MRI, SPECT and PET.

Further background is described in the following documents:

Miura et al. "Biodistribution and Toxicity of 2,4-Divinyl-nido-o-carboranyldeuteroporphyrin IX in mice" *Biochemical Pharmacology*, Vol. 43, No. 3, pp 467-476, (1992).

Miura et al. "Synthesis of a Nickel Tetracarbonanylphenylporphyrin for Boron Neutron-Capture Therapy: Biodistribution and Toxicity in Tumour-Bearing Mice" *Int. J. Cancer*, 68, pp 114-119, (1996).

Miura et al. "Boron Neutron Capture Therapy of a Murine Mammary Carcinoma using a Lipophilic Carboranyltetraphenylporphyrin" *Radiation Research*, 155, pp 603-610, (2001).

Miura et al. "Synthesis of copper octabromotetracarboranylphenylporphyrin for boron neutron capture therapy and its toxicity and biodistribution in tumour-bearing mice" *The British Journal of Radiology*, 77, pp 573-580, (2004).

An object of the present invention is to provide alternative cancer therapy. An aim of certain embodiments is to provide improved therapy in which a compound is used in the treatment of cancer using radiation therapy that will extend the period of time between administrations of the doses of the compound.

INVENTION

Accordingly, the present invention uses a compound of the formula:

(1)

wherein:
R¹, R², R³ and R⁴ are selected from an electron-withdrawing group, —NO₂, —NH₂, halogen and a substituent represented by the following formula (2)

wherein Y can be on the ortho, meta or para position on the phenyl rings and is selected from hydrogen, hydrocarbyl, non-aromatic carbocyclic, non-aromatic heterocyclic, aryl, alkylaryl, arylalkyl; or
a hydrocarbyl, non-aromatic carbocyclic, non-aromatic heterocyclic, aryl, alkylaryl or a arylalkyl group substituted with 1 to 4 hydrophilic groups selected from hydroxy, alkoxy, —C(O)OR⁵, —SOR⁶, —SO₂R⁶, nitro, amido, ureido, carbamato, —SR⁷, —NR⁸R⁹ or poly-alkyleneoxide; or a substituent represented by formula (3)

—X—(CR¹⁰R¹¹)ᵣ—Z    (3);

provided that at least one of R¹, R², R³ and R⁴ is the substituent represented by formula (2) wherein Y represents formula (3);
wherein:
X is selected from oxygen or sulfur;
R⁵, R⁶, R⁷, R⁸, R⁹, R¹⁰ and R¹¹ are selected from hydrogen and C₁ to C₄ hydrocarbyl;
Z is a carborane cluster comprising at least two carbon atoms and at least three boron atoms, or at least one carbon atom and at least five boron atoms, within a cage structure;
r is 0 or an integer from 1 to 20;
a represents an integer from 1 to 4; and
provided also that at least one of R¹, R², R³ and R⁴ is an electron withdrawing group, —NO₂, —NH₂ or halogen; and
M is selected from two hydrogen ions, a single monovalent metal ion, two monovalent metal ions, a divalent metal ion, a trivalent metal ion, a tetravalent metal ion, a pentavalent metal ion or a hexavalent metal ion, wherein the porphyrin-metal complex derived from a single monovalent metal ion is charge-balanced by a counter cation, and the porphyrin-metal complex derived from a trivalent, tetravalent, pentavalent or hexavalent metal ion is charge-balanced by an appropriate number of counter anions, dianions or trianions.

The invention provides the compound for use in cancer treatment by radiation therapy by administration of a single dose of the compound not more often than once every two weeks.

The invention further provides a method of treating cancer, comprising administering an effective dose of the compound to a patient and irradiating the patient wherein a single dose is administered not more often than once every two weeks.

According to the present invention there is thus provided the above identified compound for use in treatment of cancer by radiation therapy by administration of a single dose of the compound not more often than once every 2 weeks, 3 weeks, 4 weeks, 5 weeks, 6 weeks, 7 weeks, 8 weeks, 9 weeks, 10 weeks, 11 weeks or 12 weeks. Suitably, the single dose is administered not more often than once every 3 to 9 weeks or not more often than once every 5 to 8 weeks.

Administration of a single dose according to such a regime is significantly less distressing for the patient, with reduction in the risk of infection for the patient if they do not have to have a dose of the compound delivered frequently, e.g. every day or so. Further, treatment can be less expensive because a specialist does not have to be on hand to administer the compound daily.

The single dose can be delivered in a small number of partial doses, for convenience in balancing achieving administration of the dose against the inconvenience to the patient e.g. of receiving a large amount of injection volume at one time or of receiving a dose with potential side effects at one time. The individual partial doses may be separated in time, but are regarded as a single dose.

The less frequently the compound is administered to the patient the more benefits are potentially realised by the patient and the institution providing the treatment.

According to the present invention there is further provided the use of the aforementioned compound in the treatment of cancer by radiation therapy such that a single dose of the compound is administered for the entire course of the treatment.

Preferably, the entire course of treatment is the period determined by the clinician to be a suitable length of time to treat the cancer and/or the maximum length of treatment that the patient can sustain the treatment in one prolonged period. For example, the entire course of treatment can take at least a week, or at least 2 weeks and can take up to 16 weeks, e.g. from 1 to 16 weeks, from 3 to 12 weeks, from 4 to 9 weeks or from 5 to 8 weeks.

A single dose for the entire course of treatment will significantly improve the quality of life of the patient, who will not have to endure repeated administration of the compound in the course of treatment. Further, the cost benefits to the medical institution will be significant, as a specialist will not need to be on hand to administer the drug on a more regular basis.

According to a further aspect of the invention the aforementioned compound is for use in the treatment of cancer by radiation therapy such that a therapeutically effective amount of active agent is retained in the tumour tissue after administration of a single dose of the compound for a clinically relevant period to allow a course of radiation therapy for the clinically relevant period.

It has been found that the compound of the present invention has a significant half-life in the tumour such that active agent (which may be the compound or an active metabolite or derivative thereof) is maintained at a therapeutically effective level for a prolonged and clinically relevant period of time. This allows the patient to be administered with the compound on a less frequent basis than suggested by the known art.

Preferably, the clinically relevant period is any period during which radiation therapy can still be given to the patient or needs to be given to the patient to treat the cancer. Preferably, the clinically relevant period will be at least a week, or at least 2 weeks and can take up to 16 weeks, e.g between 1 and 16 weeks, 3 and 12 weeks, 4 and 9 weeks or 5 and 8 weeks.

The present invention is useful in embodiments for treatment of brain, head and/or neck cancer. In tests carried out in animal models, compounds of the invention have shown acceptable efficacy in treatment of squamous cell carcinoma and of adenocarcinoma. Brain, head and/or neck cancers are known to be particularly receptive to radiation therapy. Preferably, the radiation therapy is provided by X-ray and the compound is for use as an X-ray sensitizer. However, other forms of radiation therapy can be used, for example, stereotactic radiotherapy, neutron beam therapy, proton beam therapy, intensity modulated radiation therapy, 3D-conformal radiation therapy.

The radiation dose is selected to be effective in the treatment. Doses are typically 20 Gy or more, 30 Gy or more, from 20 to 80 Gy, 30 to 70 Gy, 20 to 50 Gy or 50 to 80 Gy. In typical clinical use, the dose may be given as repeated approximately similar doses, daily over a period of weeks, accumulating a total dose over the whole period. For example, in one treatment of a human patient, a dose of 2 Gy is given every day, five days per week (not at the weekends) for seven weeks, giving a total accumulated dose of 70 Gy. In testing of the invention in animal models, using once-off doses, compounds of the invention showed efficacy at doses of 25 Gy and 32 Gy.

The single dose of the compound (which can as mentioned be in multiple sub-doses) can be between 2 and 50 mg of compound/kg of patient, between 3 and 36 mg of compound/kg of patient, or between 6 and 24 mg of compound/kg of patient. In one example being investigated, the single dose is about 12 mg of compound/kg of patient.

The single dose is generally administered shortly before irradiation commences. Thus irradiation may start within the first to fourth days of administering the dose, or within the first and second day. The dose needed for each course of radiation may have adverse effects or events associated with dosing all at the same time, which may be unpleasant for the patient and, therefore, the administration of the single dose can be split over two or more sessions. Treatment generally begins after the whole of the single dose has been received.

The compound of the present invention accumulates in the tissue to be irradiated over a period of time after the administration. Optionally, commencement of radiation therapy is delayed for a short period of time to allow this accumulation and to allow clearance from the blood. Preferably, the short period of time is between 1 and 7 days, more preferably, 2 to 3 days. As the invention provides for administration of a single dose of the compound that remains active over an extended time period as described there is generally little disadvantage in further delay, if necessary, before irradiation is commenced.

Known methods and means of administration are generally suitable, for example the single dose can be administered by systemic injection or infusion. The single dose is conveniently administered in a pharmaceutically acceptable carrier.

In a further embodiment, the compound is for use in the treatment of cancer by radiation therapy characterised in that a single dose of the compound is administered for the entire course of the treatment.

The invention also provides a method of treatment of cancer comprising administering the compound and irradiating the patient, characterised in that a single dose of the compound is administered for the entire course of the treatment.

In a still further embodiment, the compound is for use in the treatment of cancer by radiation therapy characterized in that a therapeutically effective amount of X-ray sensitizing compound is retained in the tumour tissue after administration of a single dose of the compound for a clinically relevant period to allow a course of radiation therapy for the clinically relevant period.

The invention also provides a method of treatment of cancer comprising administering the compound and irradiating the patient, characterised in that a therapeutically effective amount of X-ray sensitizing compound is retained in the tumour tissue after administration of a single dose of the compound for a clinically relevant period to allow a course of radiation therapy for the clinically relevant period.

Porphyrins are not only useful in the treatment of tumours, but these compounds are also useful in the visualization and diagnosis of tumours. A porphyrin molecule has the advantage of having the ability to chelate metal ions in its interior. Such chelated porphyrins can additionally function as visualization tools for real-time monitoring of porphyrin concentration and/or diagnostic agents. For example, when chelated to paramagnetic metal ions, porphyrins may function as contrast agents in magnetic resonance imaging (MRI), and when chelated to radioactive metal ions, porphyrins may function as imaging agents for single photon emission computed tomography (SPECT) or positron emission tomography (PET).

Accordingly, the invention further provides the compound as defined herein for use in imaging a tumour by administration of a single dose not more often than once every two weeks. The invention further provides a method of imaging a tumour in a patient, comprising administering an effective dose of the compound to a patient and imaging the tumour, wherein a single dose is administered not more often than once every two weeks. There is thus provided the above-identified compound for use in imaging a tumour, e.g. cancer, by administration of a single dose of the compound not more often than once every 2 weeks, 3 weeks, 4 weeks, 5 weeks, 6 weeks, 7 weeks, 8 weeks, 9 weeks, 10 weeks, 11 weeks or 12 weeks. Suitably, the single dose is administered not more often than once every 3 to 9 weeks or 5 to 8 weeks. Specifically, a single dose can be given and then multiple imaging carried out on different days over an extended period based on that single dose of imaging agent.

Advantageously, in these imaging embodiments of the invention, frequent and/or repeated imaging can be carried out without the need for repeated doses of a contrast agent or other imaging agent. In certain clinical situation, e.g. in trials, scans have to be performed with high frequency, and this is now facilitated whilst avoiding the distress of repeated dosing with the imaging agent.

Compounds of the invention are preferably radiosensitisers which when administered to the patient make the tumour more sensitive to radiotherapy.

In all aspects of the invention compounds of the general formula (1) are provided. In embodiments, at least one of $R^1$, $R^2$, $R^3$ and $R^4$ is a halogen. The halogen can be selected from chlorine, fluorine, bromine and iodine, and is preferably bromine.

At least one of $R^1$, $R^2$, $R^3$ and $R^4$ can be selected from —$NO_2$ and Formula (2). In certain embodiments of the invention, at least two of $R^1$, $R^2$, $R^3$ and $R^4$ are selected from —$NO_2$ and formula (2). For example, two of $R^1$, $R^2$, $R^3$ and $R^4$ can be —$NO_2$ and two of $R^1$, $R^2$, $R^3$ and $R^4$ can be Formula (2) or two of $R^1$, $R^2$, $R^3$ and $R^4$ are a halogen.

In particular embodiments, $R^1$ and $R^3$ are $NO_2$ and $R^2$ and $R^4$ are Formula (2).

In embodiments of the invention $R^1$ and $R^3$ are in trans positions.

Y is suitably a hydrocarbyl. The hydrocarbyl can be a straight chain or branched hydrocarbyl group containing 1 to 20 carbon atoms including, optionally, up to three double or triple bonds. Preferably the hydrocarbyl group is selected from methyl, ethyl, n-propyl, iso-propyl, n-butyl, iso-butyl, sec-butyl, tert-butyl, propenyl, 2-butenyl, 3-butenyl, 3-butynyl, 2-methyl-2-butenyl, n-pentyl, dodecyl, hexadecyl, octadecyl and eicosyl.

The hydrocarbyl group may be unsubstituted or substituted with as many hydrophilic groups that the hydrocarbyl group can tolerate, preferably between 1 and 4. Preferably the hydrophilic group is selected from hydroxy, alkoxy, —C(O)OR$^5$, —SOR$^6$, —SO$_2$R$^6$, nitro, amido, ureido, carbamato, —SR$^7$, —NR$^8$R$^9$ and poly-alkyleneoxide. Preferably, R$^5$, R$^6$, R$^7$, R$^8$ and R$^9$ are independently selected from hydrogen and hydrocarbyl groups as defined above, except that the hydrocarbyl groups for R$^5$, R$^6$, R$^7$ and R$^8$ contain 1 to 4 carbon atoms.

The carbon atoms of the hydrocarbyl group may also be substituted with 1 to 4 heteroatoms. Herein, heteroatoms are O, S, N or NR$^{10}$. R$^{10}$ is selected from hydrogen and hydrocarbyl groups as defined above. The heteroatoms are generally not adjacent, and are preferably separated from each other by at least one carbon atom. Preferably, there is no more than one heteroatom for each two carbon atoms.

Y can be a non-aromatic carbocyclic or heterocyclic ring. Preferably, the non-aromatic carbocyclic or heterocyclic ring is a 4-, 5-, 6-, 7- or 8-membered carbocyclic or heterocyclic ring. The ring may be saturated or may contain as many unsaturated (i.e., double or triple) bonds as a carbocyclic ring can tolerate.

The saturated carbocyclic ring may be selected from cyclobutane, cyclopentane, cyclohexane and cyclopentane rings. Preferably, the unsaturated carbocyclic ring is selected from cyclobutene, cyclopentene, cyclohexene and 1,3-cycloheptadiene rings.

Preferably, Y is a heterocyclic ring. Preferably, the heterocyclic ring comprises as many heteroatoms, i.e. O, S, N or NR$^{10}$, as the heteroatom can tolerate, e.g. 1 to 4. Preferably the saturated and unsaturated non-aromatic heterocyclic ring is selected from pyrrolidinyl, piperidine, piperazine, tetrahydrofuran, furan, thiophene, 1,3-oxazolidine, imidazole and pyrrole rings. Preferably, the heterocyclic ring may be optionally substituted with hydrocarbyl as defined above, or with 1 to 4 hydrophilic groups, also as defined above.

Y can be a non-aromatic carbocyclic or heterocyclic ring. Preferably, the non-aromatic carbocyclic or heterocyclic ring may be a bicyclic ring. Preferably the carbocyclic ring is selected from bicyclo[2.2.2.]octane, bicyclo[3.1.1.]heptane, bicyclo[3.3.0.]octane and bicyclo[4.3.0.]non-3-ene. Preferably the non-aromatic heterocyclic ring is selected from 1,4 azabicyclo[2.2.2.]octane and 2-azabicyclo[3.1.1.] heptane.

Y can be an aryl group. Preferably, the aryl group can be either aromatic carbocyclic or heterocyclic group. An aromatic carbocyclic ring is preferably phenyl. The aryl ring may be optionally substituted with hydrocarbyl as defined above to produce alkylaryl or arylalkyl groups. Preferably, the aryl, alkylaryl and arylalkyl group may be substituted with 1 to 4 hydrophilic groups, as defined above.

Y may be an aromatic heterocyclic ring. Preferably, the aromatic heterocyclic ring comprises 1 to 4 heteroatoms, i.e. O, S, N or NR$^{10}$. Preferably the ring is typically 5-, 6- or 7-membered. Preferably, the aromatic heterocyclic ring is selected from thiophene, pyridine, oxazole, thiazole, oxazine and pyrazine rings. The aromatic heterocyclic ring may be substituted with 1 to 4 hydrophilic groups, as defined above.

Preferably any of the above rings may also be fused to 1 to 3 additional 5-, 6- or 7-membered aryl rings. Preferably the fused rings are selected from napthalene, anthracene, phenanthrene, triphenylene, chrysene, indoline, quinoline and tetraazanaphthalene (pteridine) rings.

Y can be an alkoxy group. Preferably, the alkoxy group contains a hydrocarbyl portion as defined above. Preferably the alkoxy groups are selected from methoxy, ethoxy, propoxy, n-butoxy, t-butoxy and dodecyloxy.

Y can be a polyalkylene oxide. Preferably, the polyalkylene oxide is defined according to the formula —(CH$_2$)$_d$—O—[(CH$_2$)$_e$—O—]$_x$—[(CH$_2$)$_f$—O—]$_y$—(CH$_2$)$_g$—OR', wherein, independently, d is 0, or an integer from 1 to 10, e is 0, or an integer from 1 to 10, f is 1 to 10, g is 1 to 10, x and y are each independently 1 or 0, and R' is either H or a hydrocarbyl group as defined previously, provided that when e is 0, then x is 0; when f is 0, then y is 0; when e is not 0, then x is 1; and when f is not 0, then y is 1.

Preferably the polyalkylene oxide is polyethylene oxide. Polyethylene oxide is defined according to the formula —(CH$_2$)$_d$—O—[(CH$_2$)$_e$—O—]$_x$—[(CH$_2$)$_f$—O—]$_y$—(CH$_2$)$_g$—OR', wherein, independently, d is 0 or 2, e is 0 or 2, f is 0 or 2, g is 2, x and y are each independently 1 or 0, and R' is either H or an ethyl group, provided that when e is 0, then x is 0; when f is 0, then y is 0; when e is not 0, then x is 1; and when f is not 0, then y is 1.

In preferred embodiments of the invention, Y is in the meta position.

M can be a monovalent ion and may be selected from Li$^{+1}$, Na$^{+1}$, K$^{+1}$, Cu$^{+1}$, Ag$^{+1}$, Au$^{+1}$ and Tl$^{+1}$. Preferably M is copper. When M is a single monovalent metal ion, the resulting porphyrin-metal complex anion is charge-balanced by a counter cation. Preferably the counter cation is selected from any of the foregoing monovalent metal ions, and ammonium and phosphonium cations. Preferably the counter cation is selected from tetramethylammonium, tetrabutylammonium, tetraphenylammonium, tetramethylphosphonium, tetrabutylphosphonium and tetraphenylphosphonium. The counter cation may be either bound or associated in some form with the porphyrin-metal complex.

M can be a divalent metal ion. Preferably the divalent metal ion is selected from V$^{+2}$, Mn$^{+2}$, Fe$^{+2}$, Ru$^{+2}$, Co$^{+2}$, Ni$^{+2}$, Cu$^{+2}$, Pd$^{+2}$, Pt$^{+2}$, Zn$^{+2}$, Ca$^{+2}$, Mg$^{+2}$, Sr$^{+2}$ and Ba$^{+2}$.

M can be a trivalent metal ion. Preferably the trivalent metal ion is selected from Gd$^{+3}$, Y$^{+3}$, In$^{+3}$, Cr$^{+3}$, Ga$^{+3}$, Al$^{+3}$, Eu$^{+3}$ and Dy$^{+3}$.

M can also be a tetravalent metal ion. Preferably the tetravalent metal ion is selected from Tc$^{+4}$, Ge$^{+4}$, Sn$^{+4}$ and Pt$^{+4}$.

M can be a pentavalent metal ion. Preferably the pentavalent metal ion is Tc$^{+5}$.

M may also be a hexavalent metal ion. Preferably the hexavalent metal ion is selected from W$^{+6}$, Tc$^{+6}$ and Mo$^{+6}$.

Preferably, M is a divalent or trivalent metal ion.

Preferably, the resulting porphyrin-metal complex cation is charge-balanced by an appropriate number of counter anions, which may be monoanions, dianions or trianions. Preferably a porphyrin-metal complex cation derived from a trivalent metal ion may be charge-balanced by a single counter monoanion, and such a complex derived from a tetravalent metal ion may, preferably, be charge-balanced by a single counter dianion or two counter monoanions, and so on.

Suitable counter monoanions include chloride, perchlorate, sulfate, nitrate and tetrafluoroborate. Preferably the counter dianion is selected from oxide, sulfide or a porphyrin compound containing a divalent negative charge. The porphyrin compound containing a divalent negative charge may be a porphyrin compound of the present invention with the proviso that M is absent. Preferably the counter trianion is phosphate.

The counter monoanion, dianion or trianion may be either bound or associated in some form with a carborane-containing porphyrin compound of the present invention. Preferably the carborane-containing porphyrin compound may also be bound to or associated with neutrally charged molecules, such as molecules of solvation, for example, water, acetonitrile, methanol and so on.

M can be a radioactive metal ion imageable by single photon emission computed tomography (SPECT) or positron emission tomography (PET). Some examples of radioactive metals suitable for SPECT are $^{67}$Cu, $^{99m}$Tc, $^{111}$In, and those for PET include $^{64}$Cu, $^{55}$Co. Preferably M is a radioactive metal useful as a radiopharmaceutical for therapy. Some examples of radioactive metals suitable for such therapy include $^{90}$Y, $^{188}$Re and $^{67}$Cu.

M is suitably a paramagnetic metal ion detectable by magnetic resonance imaging (MRI). Preferably the paramagnetic metal ion is selected from Mn, Fe, Co and Gd.

Preferably $R_{10}$ and $R_{11}$ are hydrogen.

Preferably r is 1 to 10, more preferably 1 to 6, more preferably 1.

Preferably a is 2 or 1, more preferably 1.

Z is preferably selected from the carboranes —$C_2HB_9H_{10}$ or —$C_2HB_{10}H_{10}$, wherein —$C_2HB_9H_{10}$ is nido ortho-, meta- or para-carborane, and —$C_2HB_{10}H_{10}$ is closo ortho-, meta- or para-carborane. Z can comprise 2 carbon atoms and 10 boron atoms within a cage structure.

In one particular embodiment, two of $R^1$, $R^2$, $R^3$ and $R^4$ are substituents represented by formula (2); a is 1; Y is represented by —X—$(CR^{10}R^{11})_r$—Z; $R^{10}$ and $R^{11}$ are H; r is 1; Z is —$C_2HB_{10}H_{10}$; the —X—$(CR^{10}R^{11})_r$—Z substituents are in the meta positions of the phenyl rings; the two $R^1$-$R^4$ not represented by formula (2) are —$NO_2$ or —Br; and the substituents represented by formula (2) are in the cis conformation on the porphyrin ring.

In another particular embodiment, two of $R^1$, $R^2$, $R^3$ and $R^4$ are substituents represented by formula (2); a is 1; Y is represented by —X—$(CR^{10}R^{11})_r$—Z; $R^{10}$ and $R^{11}$ are H; r is 1; Z is —$C_2HB_{10}H_{10}$; the —X—$(CR^{10}R^{11})_r$—Z substituents are in the meta positions of the phenyl rings; the two $R^1$-$R^4$ not represented by formula (2) are —$NO_2$ or —Br; and the substituents represented by formula (2) are in the trans conformation on the porphyrin ring.

When the porphyrin compound requires a counter dianion, the counter dianion may be a porphyrin compound containing a divalent negative charge. The porphyrin compound containing a divalent negative charge may be a carborane-containing porphyrin compound of the present invention, with the proviso that M is absent.

In a specific embodiment, described in more detail below, the compound is copper meso-5,15-bis[3-[(1,2-dicarba-closo-dodecaboranyl)methoxy]phenyl]-meso-10,20-dinitroporphyrin (="MTL005").

In use, it has been found that the boron-containing porphyrins of the present invention selectively accumulate in neoplasms in higher concentration and with higher tumour to normal brain and blood boron ratios than other clinically used boron-containing compounds.

Additionally, porphyrin compounds of the present invention have been tested in vivo and found to be non-toxic at theoretically therapeutic effective doses. The higher selectivity and lower toxicity of the carborane-containing porphyrins of the present invention allow for the selective destruction of tumour tissue with minimal disruption of normal tissues and tissue function when irradiated.

Another advantage of the carborane-containing porphyrins of the present invention is their increased polarity, imparted through polar groups $NO_2$, $NH_2$ and halogen. The greater polarity of such groups renders the porphyrin compounds less lipophilic, which can effect a reduction of the amount of an emulsifying co-solvent during administration. Therefore, the microlocalization within the tumour cell may be improved yielding a higher relative biological effect.

In addition, when X of the porphyrins is oxygen, the ether linkages in the carborane-containing porphyrins of the present invention are more polar than carbon-carbon linkages and therefore, provide a further reduction in lipophilicity. At the same time, the ether linkages possess nearly the same resistance to hydrolysis and other forms of chemical attack as a carbon-carbon linkage.

In a specific example of the invention, described in more detail below, a compound of the invention is administered in a single dose and thereafter therapeutically effective amounts of X-ray sensitizer are found remaining in tumour tissue after extended periods of time without re-administration of the compound. Hence, a single dose of the compound can be used in conjunction with repeated irradiation. Variation of the amount of the single dose enables variation in the time between the first single dose and further single doses (if any). The invention is hence suitable for cancer treatment with either a single dose of compound and repeated irradiation or extended intervals between single doses, again with repeated irradiation, and is especially suitable for human cancer therapy.

In testing of the invention the inventors have also successfully administered the active agent by an intratumoural route. When the compound was administered using such a method the active agent was subsequently noted to have entered and been absorbed by tumour tissue.

Examples of the present invention will now be described with reference to the following figures in which:—

EXAMPLE 1

Formulations containing a compound of the invention were prepared with the following components and are as is set out in Table 1 below:

TABLE 1

| Formulation | Concentration of MTL-005 | Solvent (% v/v of total vehicle volume) | Co-Solvent (% v/v of total vehicle volume) |
|---|---|---|---|
| 1 | 50 mg/ml | DMA (80%) | Polysorbate 20 (20%) |
| 2 | 50 mg/ml | DMA (80%) | Solutol HS15 (20%) |
| 3 | 50 mg/ml | DMA (80%) | Macrogol 300 (20%) |
| 4 | 50 mg/ml | DMA (80%) | Tetraglycol (20%) |
| 5 | 50 mg/ml | DMA (60%) | Tetraglycol (40%) |
| 6 | 50 mg/ml | DMA (80%) | Polysorbate 20 (10%) & Macrogol 300 (10%) |
| 7 | 50 mg/ml | DMA (80%) | Polysorbate 20 (10%) & Propylene glycol (10%) |
| 8 | 50 mg/ml | DMA (80%) | Polysorbate 20 (10%) & Tetraglycol (10%) |
| 9 | 50 mg/ml | DMA (80%) | Solutol HS15 (10%) & Macrogol 300 (10%) |
| 10 | 50 mg/ml | DMA (80%) | Solutol HS15 (10%) & Tetraglycol (10%) |
| 11 | 75 mg/ml | DMA (90%) | Solutol HS15 (10%) |
| 12 | 75 mg/ml | DMA (80%) | Solutol HS15 (20%) |

TABLE 1-continued

| Formu-lation | Concentration of MTL-005 | Solvent (% v/v of total vehicle volume) | Co-Solvent (% v/v of total vehicle volume) |
|---|---|---|---|
| 13 | 75 mg/ml | DMA (70%) | Solutol HS15 (30%) |
| 14 | 75 mg/ml | DMA (70%) | Solutol HS15 (20%) & Macrogol 300 (10%) |
| 15 | 50 mg/ml | DMA (70%) | Solutol HS15 (30%) |
| 16 | 50 mg/ml | DMA (70%) | Solutol HS15 (20%) & Macrogol 300 (10%) |

EXAMPLE 2

Animal Tumour Model

SCCVII murine squamous cell carcinoma cells were cultured in D-MEM enriched with 10% fetal bovine serum, 1% penicillin/streptomycin and 1% L-glutamine. Only passages 1-3 were used to initiate tumours. Cells ($2 \times 10^5$ in 0.05 mL of medium) were then implanted sc into the left thighs of 20-25 g female C3H mice (Charles River Laboratories, Wilmington, Mass.).

9% CRM Formulation

MTL005 supplied by Cambridge Major Laboratory (Batch CS08-119A and assayed at 98% purity by % area) was used to make three 15 mL batches of ~3 mg/mL formulations (MX4-33). The final concentration assayed by HPLC was 2.80 mg/mL copper meso-5,15-bis[3-[(1,2-dicarba-closo-dodecaboranyl)methoxy]phenyl]-meso-10,20-dinitroporphyrin (MTL005) with 97% purity by HPLC.

Boron and MTL005 Analysis

Direct current plasma-atomic emission spectroscopy [DCP-AES] (ARL/Fisons Model SS-7) was used (detection limit: 0.1 µg B/mL) to determine boron concentrations in tissues of individual mice. Samples (50-130 mg) were digested at 60° C. with sulfuric acid:nitric acid (1:1). Triton X-100 and water were added to give final concentrations of ~50 mg tissue/mL, 15% total acid v/v and 5% Triton X-100 v/v. The reference standard for MTL005 was assayed using prompt-gamma spectroscopy at the Massachusetts Institute of Technology Reactor Prompt-Gamma Neutron Activation Facility. The concentrations of MTL005 in the EMT-6 tumour and normal tissues can be calculated from the boron concentration of the porphyrin (22.5% boron). It is known that the ether linkages between the porphyrin and carborane cages remain intact in vivo.

Porphyrin Concentration/Formulation/Batch 2.80 mg/mL MTL005/9% CRM Batch MX4-33.

Administration Protocol and Total Doses

A total dose of 150 mg/kg MTL005 was administered to mice using three intraperitoneal (i.p.) injections over an 8-hour period at 4-h intervals using 0.018 mL/gbw for each injection. Due to the large number of animals to be dosed and irradiated, it was necessary to split the animals into two equally sized groups: Groups A and B. Animals in each Group A were injected on day 7 after tumour implantation, while animals in each Group B were injected on day 8 post tumour implantation. A group of five mice, which was given MTL005, was euthanized at the time of irradiation (24-hour clearance) for boron biodistribution data in tumour, blood, liver, spleen, brain and skin. The liver and tumour of irradiated mice given MTL-005, were also assayed for boron concentration at the time of euthanasia.

Irradiations

Irradiation was carried out 1 day after the final injection of MTL005.

The animals in Group A were irradiated 8 days, and those in Groups B were irradiated 9 days after tumour implantation. Mice were anesthetized (sodium pentobarbital, ~60 µg/g i.p.) and positioned for irradiation with the tumour-bearing leg extended across a 2-cm diameter collimated irradiation port. Tumours were irradiated using a single dose fraction of 32 gy at a dose-rate of 2.0 Gy/min using a Philips RT-100 set, operating at 100 kVp and 8 mA.

Tumours were measured 2-3 times per week and the mice were killed humanely when the calculated tumour volume ($x^2y/2$, where x is the shorter surface dimension) exceeded 500 mm$^3$.

Dosimetry

Dosimetry for X-irradiation was carried out using a thimble ionization chamber applying the 1996 IPEB code of practice.

Biodistribution

Table 2 shows the boron concentrations in various tissues of the mice (mean±SD in µg/g in various tissues of mice given 150 mg/kg MTL005 in 9% CRM at 1 day after a series of 3 i.p. injections) (n=5).

Figure 1:
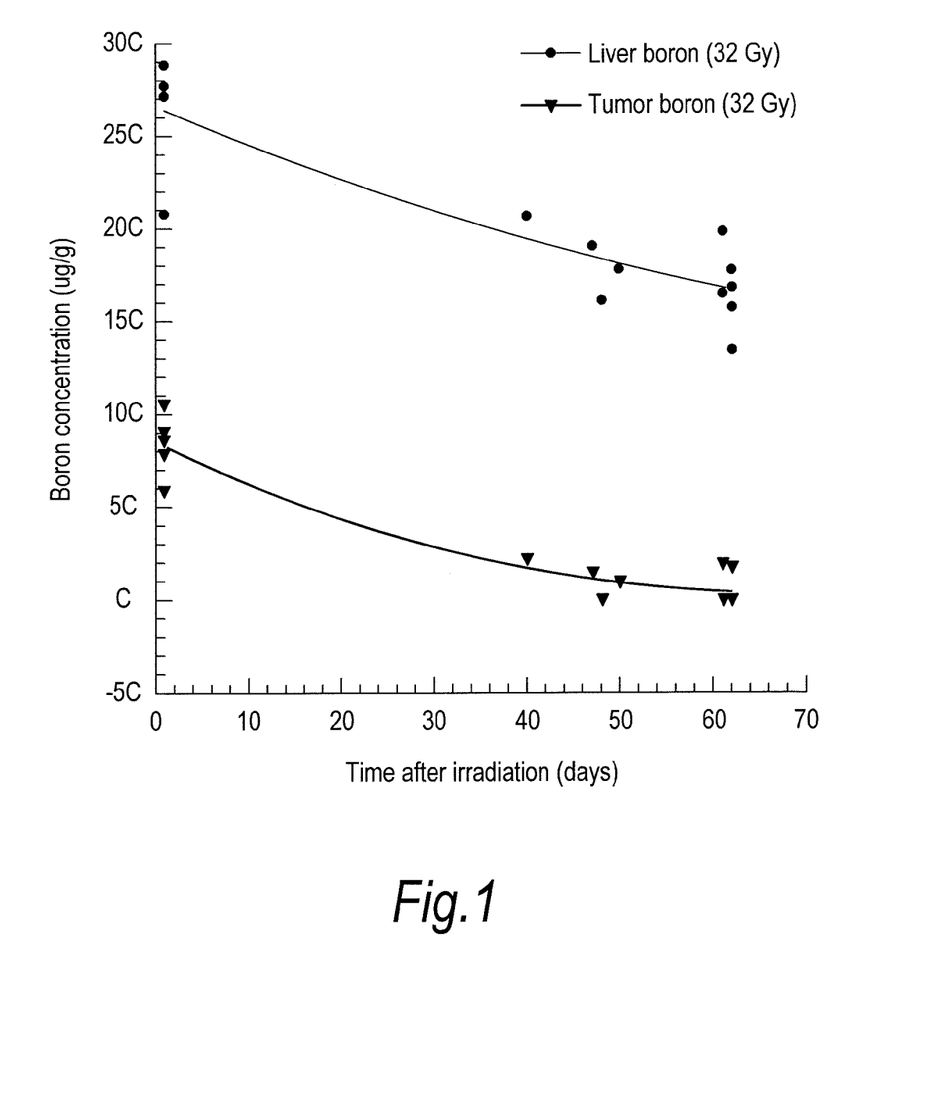
FIG. 1 shows boron concentrations in liver and tumour of mice at the time of euthanasia irradiated with 32 Gy X-rays.

The boron concentrations from livers of mice given MTL005 ranged from 135-207 µg (40-62 days post irradiation) as indicated in FIG. 1. One would have expected boron in tumour to decrease more rapidly with time. There appeared to be a constant tumour boron concentration of 9-22 µg/g in the group over the time period. There was no indication that greater survival was correlated to higher tumour boron values.

TABLE 2

| Tissue | Boron concentration (µg/g) from MXS020 |
|---|---|
| SCCVII Tumour | 83.3 ± 17.4 |
| Blood | 45.4 ± 12.2 |
| Brain | 0.8 ± 0.4 |
| Skin (pinna) | 10.3 ± 2.4 |
| Liver | 263 ± 32 |
| Spleen | 100 ± 18 |

Radiotherapy

Figure 2:
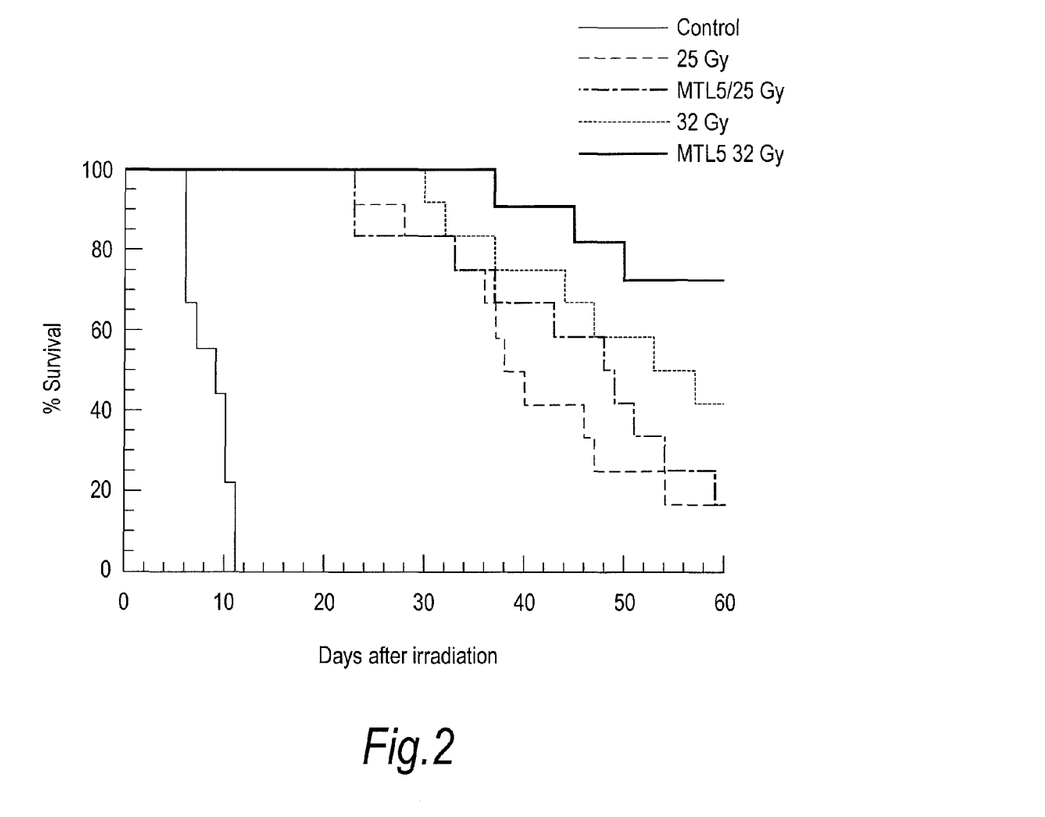
FIG. 2 shows a Kaplan-Meier graph of SCCVII squamous cell carcinomas implanted in the thighs of C3H mice treated with X-rays alone (32 Gy) or with 150 mg/kg MTL005 injected one day prior to irradiations. Mice were euthanized when the tumour volume reached 500 mm$^3$.
Figure 3:
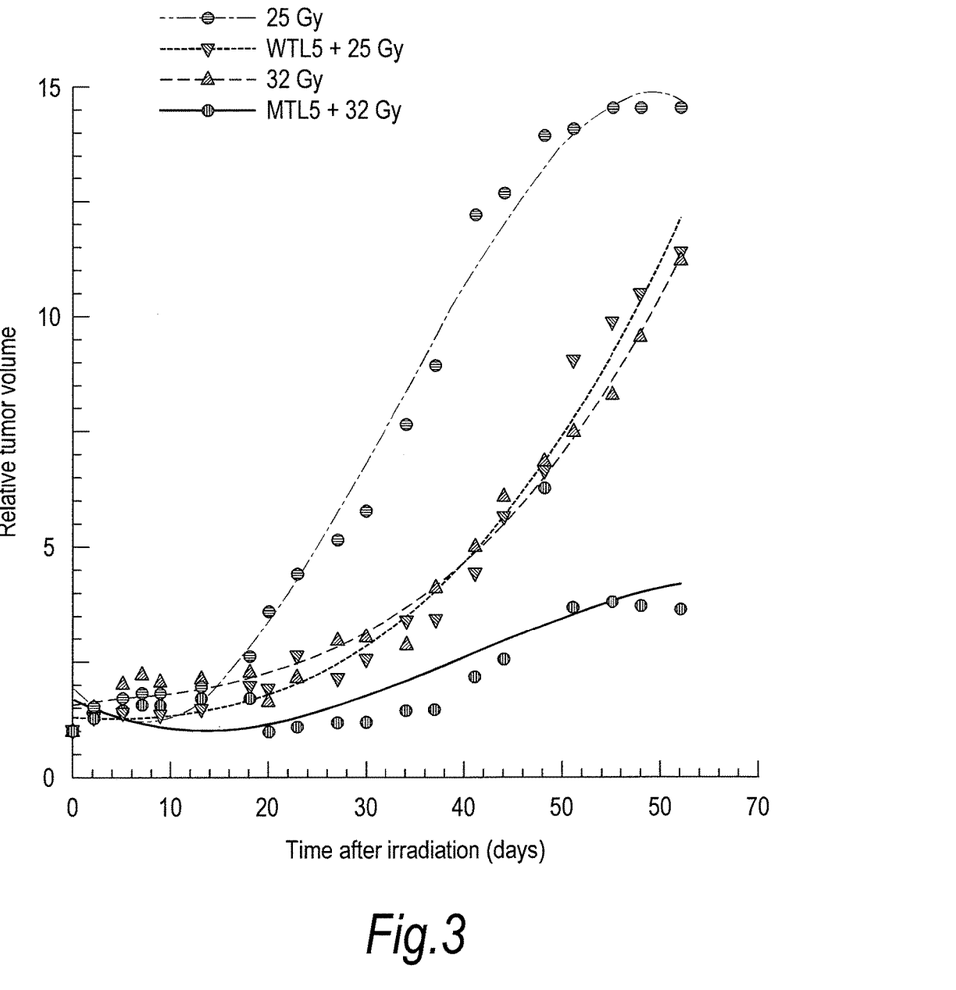
FIG. 3 shows normalized average tumour volumes over time after irradiation.

FIG. 2, shows a greater tumour control using MTL-005 than with X-rays alone. Not only were there more controlled tumours but the number of surviving mice was also higher. A Wilcoxon non-parametric two-sample test of the groups at 30 and 62 days showed that there was a significant difference (p=0.09) between the groups at 62 days.

TABLE 3

Results from irradiated and control groups in SCCVII tumour.

|  | 32 Gy only | MTL005 + 32 Gy | Untreated controls |
|---|---|---|---|
| Total mice | 12 | 11* | 9 |
| Controlled tumours** | 3 | 6 | 0 |
| Mice alive at 62 days with observable tumours | 1 | 2 | 0 |
| % Tumour control | 25 | 54.5 | 0 |

*One mouse was omitted from this study due to leg damage and was euthanized on day 48 but no tumour was observed at this time.
**Controlled tumours are defined as having a volume of 0 mm$^3$.

The number of controlled tumours was doubled in the presence of MTL-005 compared to radiation alone at 32 Gy. Further, there is still a significant concentration of active sensitiser in the tumour for days, weeks and months after the single administration of the compound.

The invention claimed is:

1. A method of treating cancer, comprising administering a compound of the formula (1) as defined below to a patient and repeatedly irradiating the patient, wherein a single dose of the compound is administered not more than once every two weeks:

wherein:
$R^1$, $R^2$, $R^3$ and $R^4$ are selected from an electron withdrawing group, —$NO_2$, —$NH_2$, halogen or a substituent represented by the following formula wherein Y can be on the ortho, meta or para position on the phenyl rings, and is selected from hydrogen, hydrocarbyl, non-aromatic carbocyclic, non-aromatic heterocyclic, aryl, alkylaryl, arylalkyl; or
a hydrocarbyl, non-aromatic carbocyclic, non-aromatic heterocyclic, aryl, alkylaryl or an arylalkyl group substituted with 1 to 4 hydrophilic groups selected from hydroxy, alkoxy, —C(O)$OR^5$, —$SOR^6$, —$SO_2R^6$, nitro, amido, ureido, carbamato, —$SR^7$, —$NR^8R^9$ or poly-alkyleneoxide; or a substituent represented by formula (3)

$$—X—(CR^{10}R^{11})_r—Z \quad (3);$$

provided that at least one of $R^1$, $R^2$, $R^3$ and $R^4$ is the substituent represented by formula (2) wherein Y represents formula (3);
wherein:
X is selected from oxygen or sulfur;
$R^5$, $R^6$, $R^7$, $R^8$, $R^9$, $R^{10}$ and $R^{11}$ are selected from hydrogen and $C_1$ to $C_4$ hydrocarbyl;
Z is a carborane cluster comprising at least two carbon atoms and at least three boron atoms, or at least one carbon atom and at least five boron atoms, within a cage structure;
r is 0 or an integer from 1 to 20;
a represents an integer from 1 to 4; and
provided also that at least one of $R^1$, $R^2$, $R^3$ and $R^4$ is an electron withdrawing group, —$NO_2$, —$NH_2$ or halogen; and M is selected from two hydrogen ions, a single monovalent metal ion, two monovalent metal ions, a divalent metal ion, a trivalent metal ion, a tetravalent metal ion, a pentavalent metal ion or a hexavalent metal ion, wherein the porphyrin-metal complex derived from a single monovalent metal ion is charge-balanced by a counter cation, and the porphyrin-metal complex derived from a trivalent, tetravalent, pentavalent or hexavalent metal ion is charge-balanced by an appropriate number of counter anions, dianions or trianions.

2. The method of claim 1, wherein the single dose is administered not more often than once every 3 to 12 weeks.

3. The method of claim 1, wherein the single dose is administered not more often than once every 4 to 9 weeks.

4. The method of claim 1, wherein the single dose is administered not more often than once every 5 to 8 weeks.

5. The method of claim 1, wherein $R^1$, $R^2$, $R^3$, $R^4$ are selected from —$NO_2$, halogen and Formula (2).

6. The method of claim 1, wherein two of $R^1$, $R^2$, $R^3$, $R^4$ are —$NO_2$ and two of $R^1$, $R^2$, $R^3$, $R^4$ are Formula (2).

7. The method of claim 1, wherein $R^1$ and $R^3$ are $NO_2$.

8. The method of claim 1, wherein $R^2$ and $R^4$ are Formula (2).

9. The method of claim 1, wherein Y is in the meta position, M is a divalent metal ion, $R^{10}$ and $R^{11}$ are hydrogen, r is 1 to 6 and a is 1 or 2.

10. The method of claim 1, wherein Z comprises 2 carbon atoms and 10 boron atoms within a cage structure.

11. The method of claim 1, wherein the compound is copper meso-5, 15-bis[3-[(1,2-dicarba-closo-dodecaboranyl)methoxy]phenyl]-meso-10,20-dinitroporphyrin.

12. The method of claim 1, comprising intra-tumoural administration of the compound.

13. The method of claim 1, comprising irradiating the patient approximately daily.

14. A method of treating cancer, comprising administering a compound of the formula (1) as defined in claim 1 to a patient and repeatedly irradiating the patient, wherein a single dose of the compound is administered for the entire course of the treatment.

15. The method claim 14, wherein the entire course of treatment takes between 1 and 16 weeks.

16. The method claim 14, wherein the entire course of treatment takes between 3 and 12 weeks.

17. The method of claim 14, wherein $R^1$, $R^2$, $R^3$, $R^4$ are selected from —$NO_2$, halogen and Formula (2).

18. The method of claim 14, wherein two of $R^1$, $R^2$, $R^3$, $R^4$ are —$NO_2$ and two of $R^1$, $R^2$, $R^3$, $R^4$ are Formula (2).

19. The method of claim 14, wherein $R^1$ and $R^3$ are $NO_2$.

20. The method of claim 14, wherein $R^2$ and $R^4$ are Formula (2).

21. The method of claim 14, wherein Y is in the meta position, M is a divalent metal ion, $R^{10}$ and $R^{11}$ are hydrogen, r is 1 to 6 and a is 1 or 2.

22. The method of claim 14, wherein Z comprises 2 carbon atoms and 10 boron atoms within a cage structure.

23. The method of claim 14, wherein the compound is copper meso-5, 15-bis[3-[(1,2-dicarba-closo-dodecaboranyl)methoxy]phenyl]-meso-10,20-dinitroporphyrin.

24. The method of claim 14, comprising intra-tumoural administration of the compound.

25. A method of treating cancer, comprising administering a single dose of a compound of the formula (1) as defined in claim 1 to a patient and repeatedly irradiating the patient, wherein a therapeutically effective amount of X-ray sensitizing compound is retained in the tumour tissue after administration of a single dose of the compound for a clinically relevant period to allow a course of radiation therapy for the clinically relevant period, wherein the clinically relevant period is any period during which radiation therapy can still be given to the patient or needs to be given to the patient to treat the cancer.

26. The method of claim 25 wherein the clinically relevant period is between 1 and 16 weeks.

27. The method of claim 25 wherein the clinically relevant period is between 4 and 9 weeks.

28. The method of claim 25, comprising intra-tumoural administration of the compound.

29. A method of imaging a tumour, comprising administration of a compound of formula (I) as defined in claim 1 not more often than once every 2 weeks, and imaging the tumour two or more times.

30. The method of claim 29, comprising intra-tumoural administration of the compound.

* * * * *

UNITED STATES PATENT AND TRADEMARK OFFICE
CERTIFICATE OF CORRECTION

PATENT NO. : 9,750,809 B2  
APPLICATION NO. : 14/413949  
DATED : September 5, 2017  
INVENTOR(S) : Christopher Beattie et al.

Page 1 of 1

It is certified that error appears in the above-identified patent and that said Letters Patent is hereby corrected as shown below:

In the Claims

Claim 15, Column 14, Line 41, "The method claim 14" should read -- The method of claim 14 --.

Claim 16, Column 14, Line 43, "The method claim 14" should read -- The method of claim 14 --.

Signed and Sealed this  
Twenty-eighth Day of November, 2017

Joseph Matal  
*Performing the Functions and Duties of the*  
*Under Secretary of Commerce for Intellectual Property and*  
*Director of the United States Patent and Trademark Office*